(12) United States Patent
Weuthen et al.

(10) Patent No.: US 7,145,001 B1
(45) Date of Patent: Dec. 5, 2006

(54) METHOD FOR PRODUCING SOLID SUGAR SURFACTANTS

(75) Inventors: Manfred Weuthen, Langenfeld (DE); Karl Heinz Schmid, Mettmann (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 746 days.

(21) Appl. No.: 10/111,863

(22) PCT Filed: Oct. 18, 2000

(86) PCT No.: PCT/EP00/10266

§ 371 (c)(1),
(2), (4) Date: Apr. 29, 2002

(87) PCT Pub. No.: WO01/30792

PCT Pub. Date: May 3, 2001

(30) Foreign Application Priority Data

Oct. 27, 1999 (DE) .................................. 199 51 598

(51) Int. Cl.
*C07H 1/00* (2006.01)
*C07H 1/06* (2006.01)

(52) U.S. Cl. ...................................... 536/127; 536/124

(58) Field of Classification Search ............... 536/127, 536/124

See application file for complete search history.

(56) References Cited

U.S. PATENT DOCUMENTS

| | | |
|---|---|---|
| 3,966,629 A | 6/1976 | Dumbrell |
| 4,062,647 A | 12/1977 | Storm et al. |
| 4,737,306 A | 4/1988 | Wichelhaus et al. |
| 4,820,439 A | 4/1989 | Rieck |
| 5,043,091 A * | 8/1991 | Joshi et al. ............. 252/174.17 |
| 5,374,716 A | 12/1994 | Biermann et al. |
| 5,417,951 A | 5/1995 | Just |
| 5,576,425 A | 11/1996 | Hill et al. |
| 5,780,420 A | 7/1998 | Breuer et al. |
| 6,030,937 A | 2/2000 | Kruse et al. |
| 6,340,665 B1 | 1/2002 | Lueder et al. |

FOREIGN PATENT DOCUMENTS

| | | |
|---|---|---|
| DE | 23 34 899 | 7/1973 |
| DE | 35 26 405 | 7/1985 |
| DE | 44 00 024 | 1/1994 |
| DE | 197 02 845 | 7/1998 |
| EP | 0 026 529 | 9/1980 |
| EP | 0 028 432 | 10/1980 |
| EP | 0 164 514 | 4/1985 |
| EP | 0 301 298 | 7/1988 |
| GB | 1 400 898 | 7/1973 |
| WO | WO 98/03977 | 4/1990 |
| WO | WO 91/08171 | 6/1991 |
| WO | WO 92/13938 | 8/1992 |
| WO | WO 97/03165 | 1/1997 |
| WO | WO 97/10324 | 9/1998 |
| WO | WO 98/40460 | 9/1998 |

* cited by examiner

*Primary Examiner*—Shaojia Anna Jiang
*Assistant Examiner*—Everett White
(74) *Attorney, Agent, or Firm*—John F. Daniels; Daniel S. Ortiz

(57) ABSTRACT

A process for making solid sugar surfactants involving: (a) providing a glycose component; (b) acetalizing the glycose component with a fatty alcohol to form a technical mixture containing excess fatty alcohol and alkyl and/or alkenyl oligoglycoside; and (c) contacting the technical mixture with an extractant to form a solid phase containing the extractant, a predominant part of alkyl and/or alkenyl oligoglycoside and a small amount of fatty alcohol, and a liquid phase containing a predominant part of the fatty alcohol.

8 Claims, No Drawings

METHOD FOR PRODUCING SOLID SUGAR SURFACTANTS

BACKGROUND OF THE INVENTION

This invention relates generally to the production of solid sugar surfactants and more particularly to an extraction process for the production of solid alk(en)yl oligoglycosides.

By virtue of their excellent performance properties and their high ecotoxicological compatibility, alk(en)yl oligoglycosides are important basic raw materials, for example for the production of cosmetic preparations or manual dishwashing detergents. These surfactants are normally processed in the form of water-containing pastes although, for a number of applications, for example the production of bar soaps or detergents, there is also a particular interest in solid preparations which are easier to process and do not first have to be freed from unwanted water.

Various processes for the production of such solid sugar surfactants are known from the prior art. For example, WO 97/03165 (Henkel) describes the simultaneous drying and granulation of zeolite-containing sugar surfactant pastes in a fluidized bed. International patent applications WO 97/10324 and WO 98/40460 (Henkel) describe the removal of water from sugar surfactant pastes in a horizontal thin-layer evaporator.

Unfortunately, these processes are of little interest on economic grounds because they involve considerable outlay on equipment. Accordingly, the problem addressed by the present invention was to provide a simplified process for the production of solid sugar surfactants which, in particular, would not involve the removal of excess fatty alcohol by distillation.

DESCRIPTION OF THE INVENTION

The present invention relates to a process for the production of solid sugar surfactants which is characterized in that glycoses are acetalized with fatty alcohols in known manner and the technical mixtures obtained, which still contain at least some excess fatty alcohol besides the alkyl and/or alkenyl oligoglycosides, are contacted with solid extractants, resulting in the formation of two phases, namely a first solid phase which contains the extractant together with by far the predominant part of the alkyl and/or alkenyl oligoglycosides and a reduced amount of fatty alcohols in relation to the starting mixture and a second liquid phase which consists predominantly of the fatty alcohol removed.

It has surprisingly been found that solid sugar surfactants distinguished by a small percentage content of free fatty alcohols can be obtained in a technically simple manner and at low cost by the process according to the invention. The products obtainable by the process generally contain 20 to 70 and more particularly 30 to 50% by weight of glycosides.

Alkyl and/or Alkenyl Oligoglycosides

Alkyl and alkenyl oligoglycosides in the context of the process according to the invention are nonionic surfactants which preferably correspond to formula (I):

$$R^1O\text{—}[G]_p \quad (I)$$

in which $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. Where mention is made of the production of these compounds in a non-critical, i.e. known, manner, reference may be made to EP-A1 0 301 298 and WO 90/03977 as representative of the extensive literature available on the subject. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut alcohol with a DP of 1 to 3 are preferred. "Technical mixtures" which are subsequently subjected to extraction are understood to be intermediate products which accumulate immediately after the acetalization step, i.e. essentially contain unreacted fatty alcohol besides the target product. It is preferred but not necessary in the process according to the invention to neutralize the acidic catalyst by adding a base before the extraction step. This may also be achieved through the choice of the extractant.

Extractants

It is recommended that the extractants be chosen from those which have a higher hydrophilia than fatty alcohols with respect to alkyl and/or alkenyl oligoglycosides and a large surface. Preferred extractants are those which, at least after adsorption of the alkyl and/or alkenyl oligoglycosides, are present in solid form at room temperature and which in particular are solid at room temperature right at the beginning of the extraction step. The following are typical examples of suitable extractants:

Zeolites. Suitable extractants are, for example, the finely crystalline, synthetic zeolites A and/or P containing bound water which are commonly used as detergent builders. A particularly preferred zeolite P is zeolite MAP® (a Crosfield product). However, zeolite X and mixtures of A, X and/or P and also Y are also suitable. Also of particular interest is a co-crystallized sodium/potassium aluminium silicate of zeolite A and zeolite X which is commercially available as VEGOBOND AX® (a product of Condea Augusta S.p.A.).

Silicates. Other suitable extractants are crystalline layer-form sodium silicates with the general formula $NaMSi_xO_{2x+1} \cdot yH_2O$, where M is sodium or hydrogen, x is a number of 1.9 to 4 and y is a number of 0 to 20, preferred values for x being 2, 3 or 4. Crystalline layer silicates such as these are described, for example, in European patent application EP 0 164 514 A1. Preferred crystalline layer silicates are those in which M in the general formula stands for sodium and x assumes the value 2 or 3. Both .- and δ-sodium disilicates $Na_2Si_2O_5 \cdot yH_2O$ are particularly preferred, .-sodium disilicate being obtainable for example by the process described in International patent application WO 91/08171. Other suitable layer silicates are known, for example, from patent applications DE 23 34 899 A1, EP 0 026 529 A1 and DE 35 26 405 A1. Their suitability for use is not confined to a particular composition or structural formula. However, smectites are preferred, bentonites being particularly preferred. Suitable layer silicates which belong to the group of water-swellable smectites are, for example, those corresponding to the following general formulae:

| | |
|---|---|
| $(OH)_4Si_{8-y}Al_y(Mg_xAl_{4-x})O_{20}$ | montmorillonite |
| $(OH)_4Si_{8-y}Al_y(Mg_{6-z}Li_z)O_{20}$ | hectorite |
| $(OH)_4Si_{8-y}Al_y(Mg_{6-z}Al_z)O_{20}$ | saponite | where x=0 to 4, y=0 to 2 and z=0 to 6. In addition, small quantities of iron may be incorporated in the crystal lattice of the layer silicates corresponding to the above formulae. By virtue of their ion-exchanging properties, the layer silicates may also contain hydrogen, alkali metal and alkaline earth metal ions, more particularly $Na^+$ and $Ca^{2+}$. The quantity of water of hydration is generally in the range from 8 to 20% by weight and is dependent upon the degree of swelling and upon the processing method. Suitable layer silicates are known, for example, from U.S. Pat. No. 3,966,629, U.S. Pat. No. 4,062,647, EP 0 026 529 A1 and EP 0 028 432 A1. Layer silicates which have been substantially freed from calcium ions and strongly coloring iron ions by an alkali treatment are preferably used. Other preferred extractants are amorphous sodium silicates with a modulus ($Na_2O$:$SiO_2$ ratio) of 1:2 to 1:3.3, preferably 1:2 to 1:2.8 and more preferably 1:2 to 1:2.6. In the context of the invention, the term "amorphous" is also understood to encompass "X-ray amorphous". In other words, the silicates do not produce any of the sharp X-ray reflexes typical of crystalline substances in X-ray diffraction experiments, but at best one or more maxima of the scattered X-radiation which have a width of several degrees of the diffraction angle. Particularly good builder properties may even be achieved where the silicate particles produce crooked or even sharp diffraction maxima in electron diffraction experiments. This may be interpreted to mean that the products have microcrystalline regions between 10 and a few hundred nm in size, values of up to at most 50 nm and, more particularly, up to at most 20 nm being preferred. So-called X-ray amorphous silicates such as these are described for example in German patent application DE-A-4400024 A1. Compacted amorphous silicates, compounded amorphous silicates and overdried X-ray-amorphous silicates are particularly preferred.

Polymers and polysaccharides. Suitable polymers are, for example, protein hydrolyzates, polyamides, polyacrylates, polyurethanes and polyvinyl pyrrolidones. Urea and polyurea are also suitable polymers. The polysaccharides may be selected, for example, from celluloses, cellulose derivatives, starches or starch hydrolyzates.

Salts of inorganic acids. Typical examples are the alkali metal and/or alkaline earth metal salts, aluminium or zinc salts of hydrochloric acid, sulfuric acid, nitric acid, phosphoric acid, boric acid and silicic acid, more particularly the alkali metal carbonates, alkali metal hydrogen carbonates, alkali metal sulfates, alkali metal borates and perborates, the various alkali metal silicates ("waterglasses") and alkali metal phosphates. Typical examples are magnesium sulfate heptahydrate or borax.

Salts of organic acids. Typical examples are the alkali metal and/or alkaline earth metal salts, aluminium or zinc salts of $C_{1-22}$ monocarboxylic acids, such as formic acid, acetic acid, propionic acid, butyric acid, valeric acid, caproic acid, caprylic acid, 2-ethylhexanoic acid. Sodium acetate is particularly preferred. The monocarboxylic acids may also be replaced by corresponding $C_{2-6}$ dicarboxylic acids so that, in the same way as above, suitable extractants are also the corresponding salts of succinic acid, maleic acid, fumaric acid, glutaric acid and adipic acid. Finally, salts of hydroxyfunctionalized polybasic carboxylic acids, for example the above-mentioned salts of malic acid, tartaric acid and in particular citric acid, may also be used. The use of alkali metal citrates is most particularly preferred. Providing the organic acids on which the salts are based are solid at room temperature, they may also be used. This applies in particular to citric acid which is a particularly preferred extractant.

The extraction step may be carried out in different ways. For example, the technical glycoside mixture may be intensively mixed with the extractant and the fatty alcohol subsequently removed by filtration. The extraction step may also be carried out using a column containing the extractant. In these variants of the process, a ratio by weight of glycoside to fatty alcohol of generally 1:2 to 50:1, preferably 2:1 to 20:1 and more particularly 5:1 to 10:1 is established. The ratio by weight of the mixture used to the extractant may be 5:1 to 1:5 and is preferably 1:1 to 2:1. Another feature common to the various embodiments of the process according to the invention is that, after the extraction step, the solid phase is preferably size-reduced and ground to the required particle size while the fatty alcohol recovered—which is of very high purity—is returned to the acetalization step.

Commercial Applications

The products obtainable by the process according to the invention are suitable, for example, for the production of solid detergents such as, for example, powders, compactates, tablets or bars, more particularly for cleaning hard surfaces, in which they may be present in quantities of 1 to 50, preferably 2 to 25 and more particularly 5 to 15% by weight, based on the particular composition.

EXAMPLES

Example 1

1 Mol (180 g) of glucose was acetalized in known manner with 4.5 mol (860 g) of $C_{12/14}$ coconut fatty alcohol in the presence of p-toluenesulfonic acid. The water of reaction was continuously removed during the condensation and the reaction was terminated when the residual glucose content had fallen below 0.5% by weight. The acidic reaction product was neutralized by addition of magnesium oxide and cooled to 60° C., followed by the addition with intensive stirring of 500 g of fine-particle cellulose. After homogenization, the mixture was filtered through a filter covered with another 100 g of cellulose. After solidification, the filter cake was ground. 980 g of product containing 33.7% by weight of coconut alkyl oligoglucoside and 15.3% by weight of fatty alcohol were obtained.

Example 2

A glass column (length 1 m, diameter 10 cm) was heated to 50° C. and filled with a mixture of soda and $C_{12/14}$ coconut fatty alcohol (ratio by weight 1:1). A neutralized reaction mixture corresponding to Example 1 was then applied. After the mixture had completely passed through, the upper half of the column was removed and, after solidification, was ground. 880 g of product containing 31.8% by weight of coconut alkyl oligoglucoside and 11.4% by weight of fatty alcohol were obtained.

The invention claimed is:

1. A process for making solid sugar surfactants comprising:
   (a) providing a glycose component;
   (b) acetalizing the glycose component with a fatty alcohol to form a technical mixture containing excess fatty alcohol and alkyl and/or alkenyl oligoglycoside; and
   (c) contacting the technical mixture with an extractant to form a solid phase containing the extractant, a predominant part of alkyl and/or alkenyl oligoglycoside and a small amount of fatty alcohol, and a liquid phase containing a predominant part of the fatty alcohol.

2. The process of claim 1 wherein the solid phase contains from about 20 to 70% by weight of alkyl and/or alkenyl oligoglycoside.

3. The process of claim 1 wherein the solid phase contains from about 30 to 50% by weight of alkyl and/or alkenyl oligoglycoside.

4. The process of claim 1 wherein the extractant has a higher degree of hydrophilia than the fatty alcohol with respect to the alkyl and/or alkenyl oligoglycoside.

5. The process of claim 1 wherein the extractant is in solid form at room temperature.

6. The process of claim 1 wherein the extractant is selected from the group consisting of a zeolite, a silicate, a polymer, a polysaccharide, an inorganic acid salt, an organic acid salt, and mixtures thereof.

7. The process of claim 1 wherein the solid phase is size-reduced and ground to a desired particle size.

8. A cleaning composition containing the solid sugar surfactant of claim 1.

* * * * *